US006896683B1

(12) United States Patent
Gadberry et al.

(10) Patent No.: US 6,896,683 B1
(45) Date of Patent: May 24, 2005

(54) SURGICAL INSTRUMENT WITH IMPROVED HANDLE ASSEMBLY

(75) Inventors: Donald L. Gadberry, Dana Point, CA (US); Hank Kahle, Trabuco Canyon, CA (US); Gary M. Johnson, Mission Viejo, CA (US); Steven R. Anderson, Las Flores, CA (US)

(73) Assignee: Applied Material Resources Corporation, Rancho Santa Margarita, CA (US)

( * ) Notice: Subject to any disclaimer, the term of this patent is extended or adjusted under 35 U.S.C. 154(b) by 157 days.

(21) Appl. No.: 09/675,851

(22) Filed: Sep. 28, 2000

Related U.S. Application Data

(63) Continuation of application No. PCT/US00/01296, filed on Jan. 19, 2000.
(60) Provisional application No. 60/117,079, filed on Jan. 25, 1999.

(51) Int. Cl.[7] .............................................. A61B 17/10
(52) U.S. Cl. ...................................... 606/142; 606/143
(58) Field of Search ................................ 606/142, 139, 606/143, 144, 213, 217, 219, 220, 221, 174, 205–208, 210; 7/125–135

(56) References Cited

U.S. PATENT DOCUMENTS

| | | |
|---|---|---|
| 2,733,441 A | 2/1956 | White |
| 3,775,826 A | 12/1973 | Reed ............................ 29/212 |
| 3,827,277 A | 8/1974 | Weston ......................... 72/410 |
| 4,166,466 A | 9/1979 | Jarvik ......................... 128/325 |
| 4,226,242 A | 10/1980 | Jarvik ......................... 128/325 |
| 4,296,751 A | 10/1981 | Blake, III et al. ........... 128/325 |
| 4,425,915 A | 1/1984 | Ivanov ......................... 128/325 |
| 4,430,997 A | 2/1984 | DiGiovanni et al. ......... 128/326 |
| 4,448,193 A | 5/1984 | Ivanov ......................... 128/326 |
| 4,452,357 A | 6/1984 | Klieman et al. ............. 206/339 |
| 4,478,220 A | 10/1984 | Di Giovanni et al. ....... 128/326 |
| 4,480,640 A | 11/1984 | Becht .......................... 128/325 |
| 4,480,641 A | 11/1984 | Failla et al. ................. 128/326 |
| 4,491,133 A | 1/1985 | Menges et al. .............. 128/326 |
| 4,522,207 A | 6/1985 | Klieman et al. ............. 128/325 |
| 4,534,351 A | 8/1985 | Rothfuss et al. ............. 128/334 |
| 4,557,263 A | 12/1985 | Green .......................... 128/325 |
| 4,616,650 A | 10/1986 | Green et al. ................. 128/325 |
| 4,616,651 A | 10/1986 | Golden ........................ 128/325 |
| 4,712,549 A | 12/1987 | Peters et al. ................. 128/325 |
| 5,049,152 A | 9/1991 | Simon et al. ................ 602/143 |
| 5,100,420 A | 3/1992 | Green et al. ................. 606/143 |
| 5,423,835 A | 6/1995 | Green et al. ................. 606/143 |
| 5,431,668 A | 7/1995 | Burbank, III et al. ....... 606/143 |
| 5,626,585 A | 5/1997 | Mittelstadt et al. .......... 606/143 |
| 5,643,291 A | 7/1997 | Pier et al. .................... 606/143 |
| 5,690,673 A | * 11/1997 | Koschet et al. .............. 606/205 |
| 5,772,673 A | 6/1998 | Cuny et al. .................. 606/142 |
| 5,810,878 A | * 9/1998 | Burel et al. .................. 606/205 |

* cited by examiner

*Primary Examiner*—Gloria M. Hale
(74) *Attorney, Agent, or Firm*—Richard L. Myers; Kenneth K. Vu

(57) ABSTRACT

A modulator clip applier includes a cartridge containing multiple surgical clips, and a handle assembly for operating the cartridge to crimp one of the clips onto body tissue of a patient. The handle assembly has a scissors configuration with a bayonet coupling, and flange pairs widely separated to provide a high degree of stability. The bayonet coupling enables the handles of the assembly to be fully separated for cleaning. Snap fittings between the cartridge and handle assembly are provided at the fulcrum and also at a spaced location where an operating pin of the cartridge engages intersecting slots in the flanges. Overdrive protection of three different types is contemplated along with a structure facilitating operation of the handle assembly by palming a pair of handle bars.

23 Claims, 17 Drawing Sheets

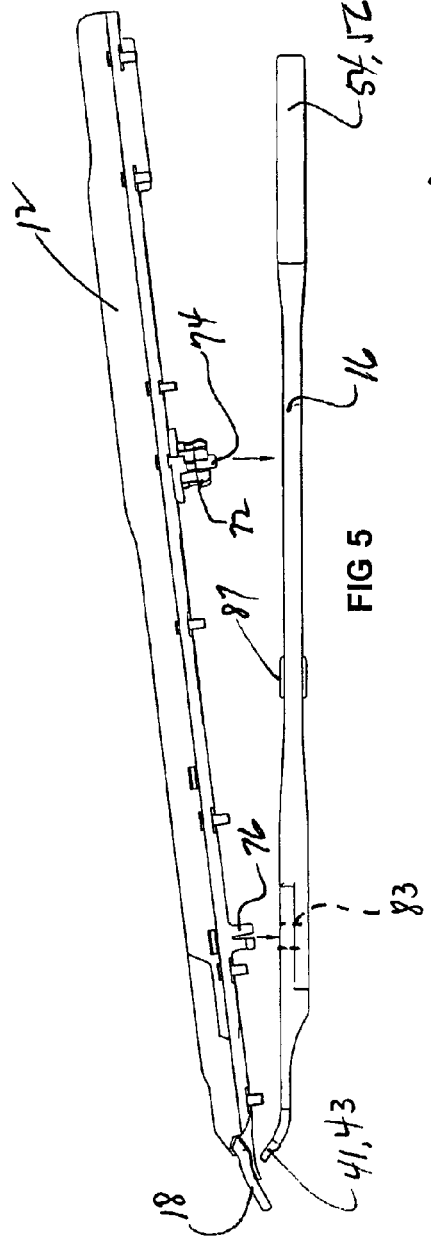
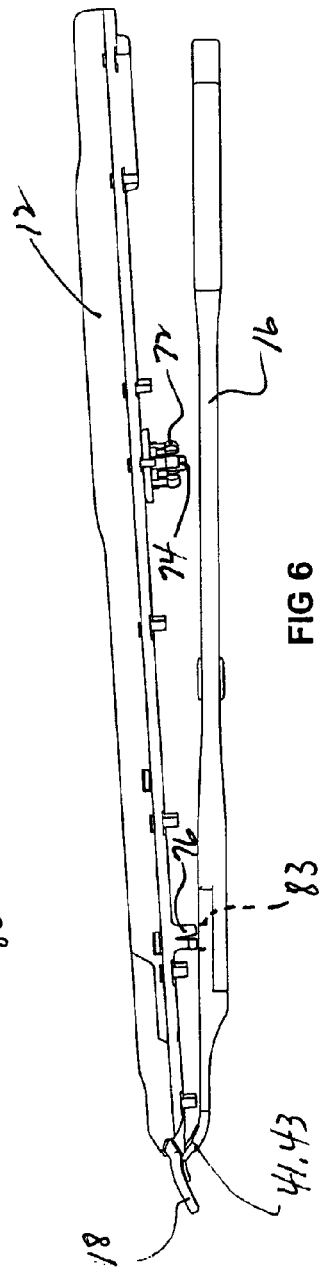
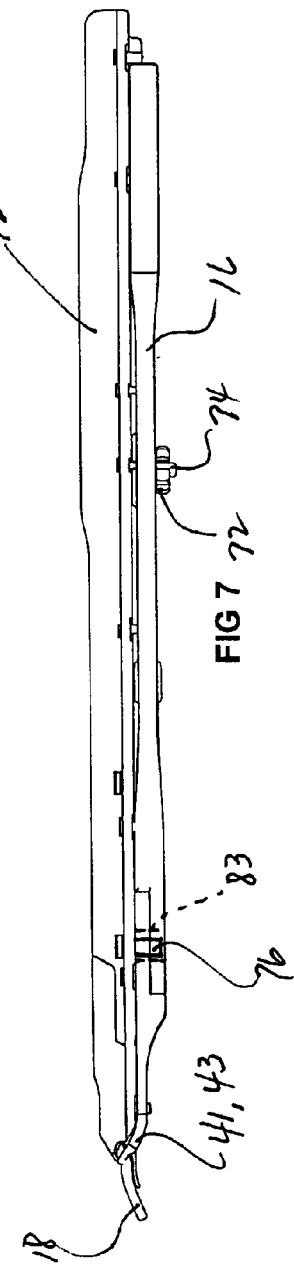
FIG 5
FIG 6
FIG 7

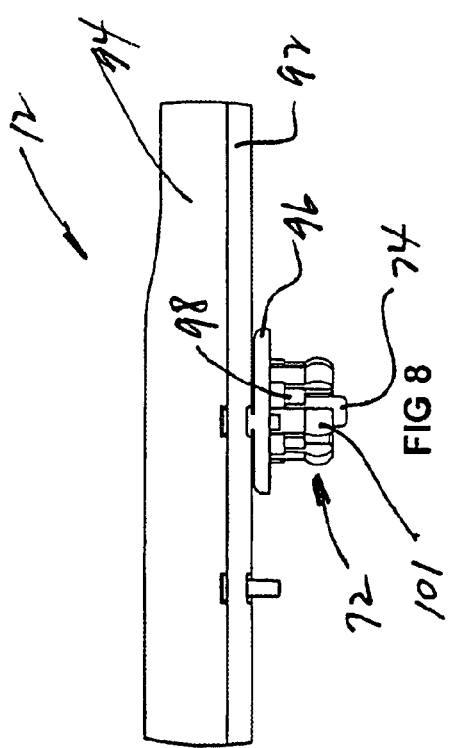
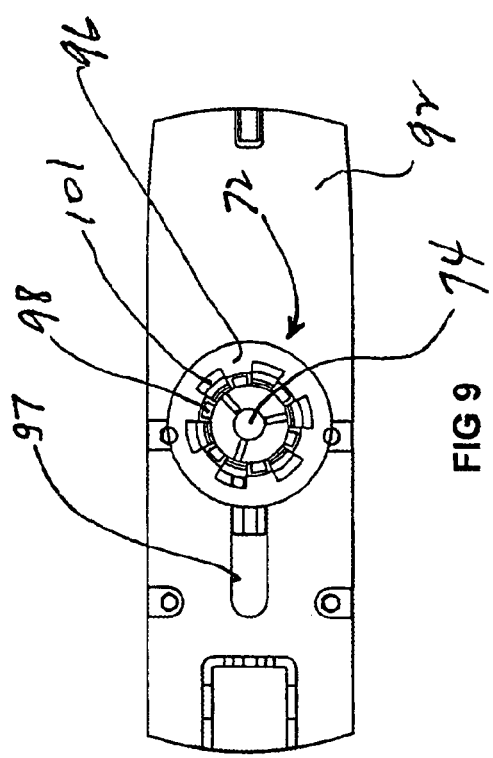

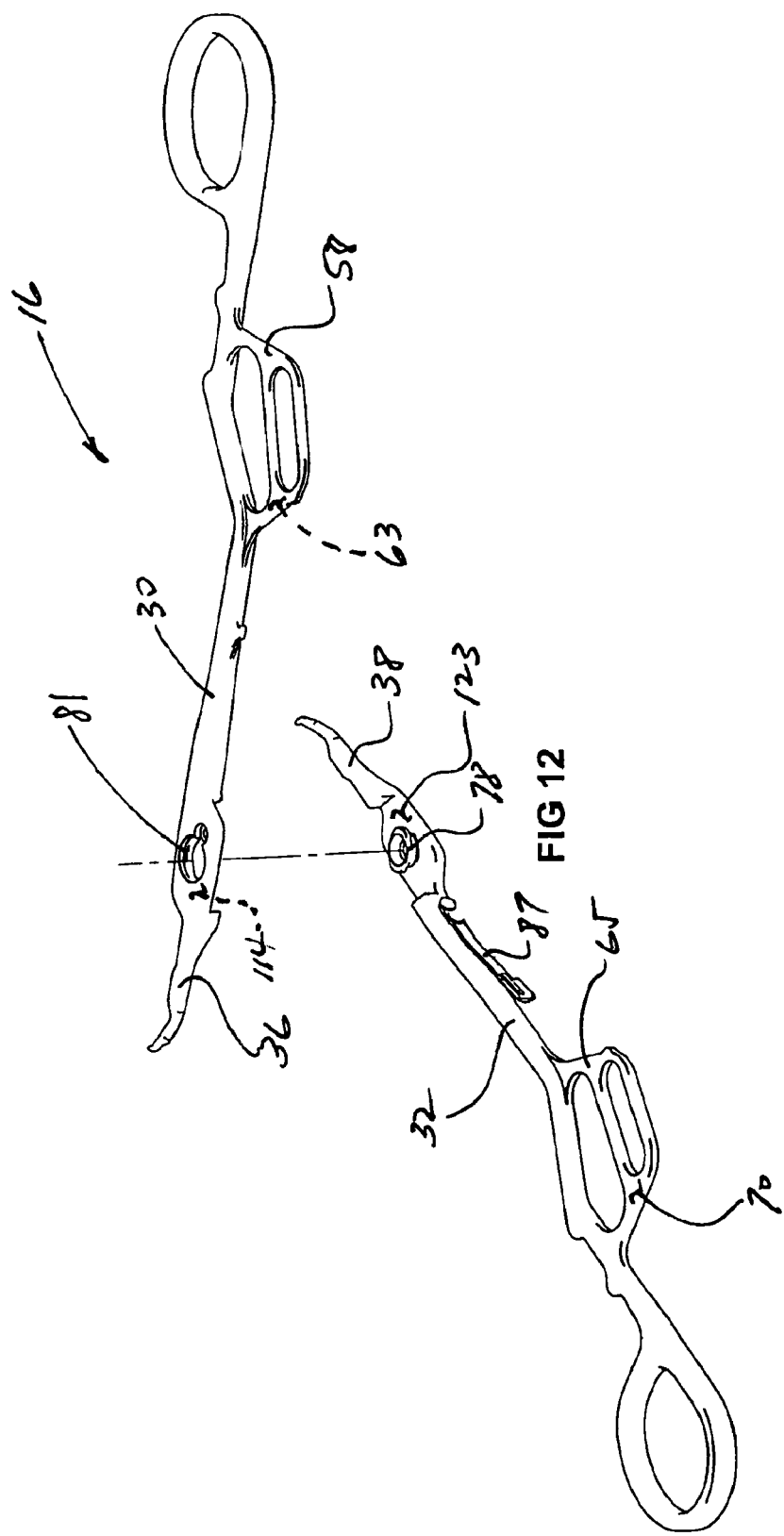

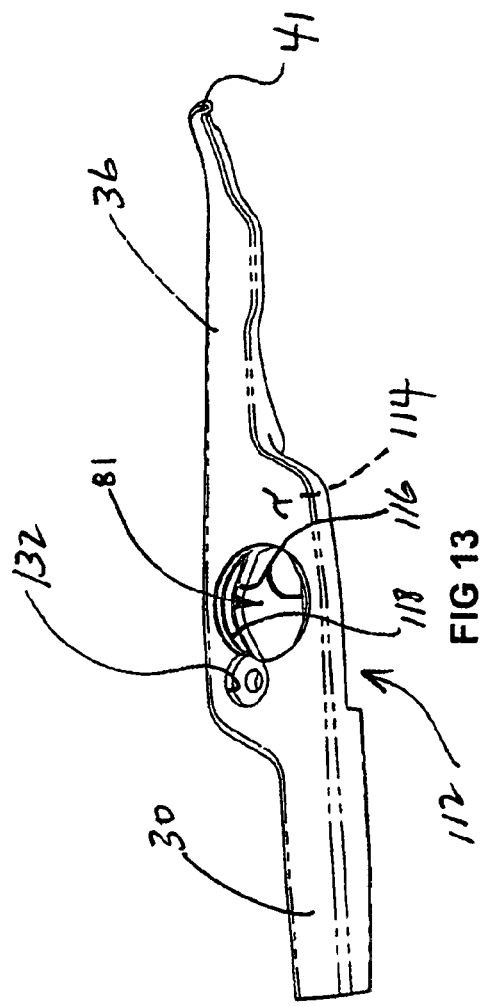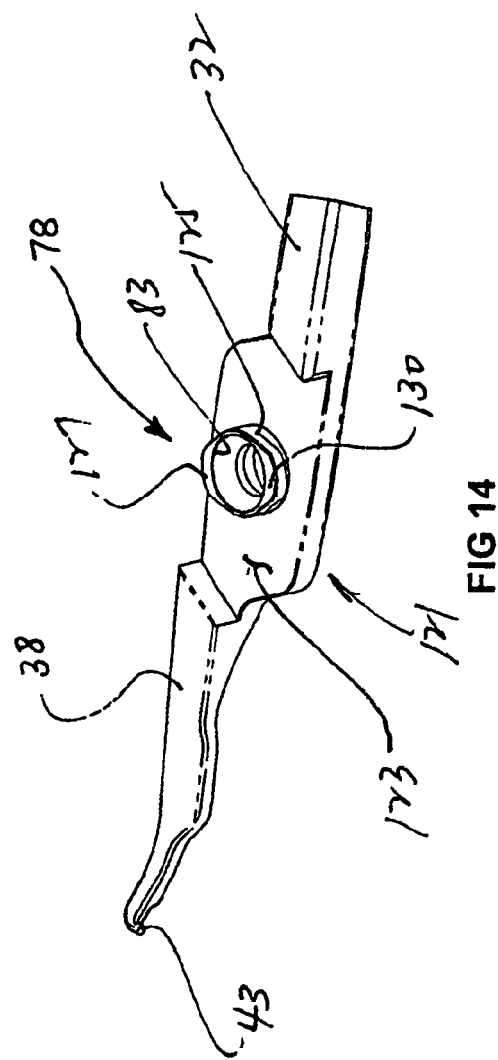

SURGICAL INSTRUMENT WITH IMPROVED HANDLE ASSEMBLY

CROSS REFERENCE TO RELATED APPLICATIONS

This application claims the U.S. Provisional Application Ser. No. 60/117,079 filed on Jan. 25, 1999, and a continuation of PCT Application Ser. No. PCT/US00/01216 filed on Jan. 19, 2000, both of which are incorporated herein by reference.

BACKGROUND OF THE INVENTION

1. Field of the Invention

This invention relates generally to surgical instruments, and more specifically to instruments having such as ligating clip appliers adapted to operate and effectors such as multiple-clip cartridges.

2. Discussion of Related Art

Surgical instrument clip appliers commonly include handles that are operable by a user to close a pair of jaws. In the case of clip applier, a ligating clip, removably mounted within the jaws, can be crimped or closed to engage tissue or occlude a body conduit such as a blood vessel. The clip is initially mounted within the jaws when the jaws are in an opened state. When the handles are operated to move the jaws to a closed state, the clip is crimped to achieve ligation. Reopening the jaws permits removal of the clip applier from the ligating clip.

Particularly in a modular clip applier it is always desirable to increase the stability of the handle assembly. With the handles disposed in a common scissors configuration, a single pivot point or fulcrum permits operation of the handles to open and close the jaws. Unfortunately, with a typical elongate configuration, the handles and jaws are spaced a considerable distance from the pivot point or fulcrum, so that the handle assembly tends to be susceptible to misalignment. When jaws become misaligned, clips cannot be closed properly and may even fall from the jaws of the assembly. Thus stability needs to be maintained along the entire travel of the jaws from the opened state to the closed state.

Particularly in a modular system wherein a disposable cartridge is to be removably attached to a non-disposable handle assembly, the attachment system is of particular concern. In the past, attachments have been made solely with a snap fitting at the fulcrum of the handle assembly. A pin carried by the cartridge has been laterally movable by the handle assembly but has been free to float vertically of the handle assembly. Accordingly, the pin has not functioned as part of the attachment system.

Box hinges have been used at the pivot point or fulcrum in an attempt to increase the stability of the handle assembly. These hinges provide larger areas of surface contact but unfortunately these areas are fairly close to the fulcrum and therefore offer very short lever arms for the maintenance of stability.

The cleaning of the handle assembly is always of interest as this is the reusable component of a modular system. While box hinges have been of some value for stability purposes, they present many hidden surfaces which are not susceptible to cleaning. Furthermore, the box hinges have functioned as permanent attachments and have not permitted complete separation of the handles.

Surgeons have commonly used clip appliers in a method called "palming" where the fingers of the surgeon are disposed along the handles distally of the finger rings. This positioning of the hand relative to the handle assembly increases tactile feedback and therefore is often preferred by the surgeon. Where the scissors configuration has included a significant angle along the handles, the surgeon's fingers and thumb have tended to slip along the handles when using this palming method.

In a modular system, the disposable cartridge is typically manufactured with molded plastic components which are not particularly amenable to close tolerances. Especially where complex linkage is involved, the need for plastic parts with closer tolerances can add significantly to manufacturing costs.

SUMMARY OF THE INVENTION

These deficiencies of the prior art are overcome with the present invention which includes a bayonet fitting disposed at the pivot point or fulcrum of the handle assembly. The bayonet fitting not only provides increased stability for the handle assembly, but also facilitates assembly of the handles and subsequent disassembly for cleaning purposes. Upon disassembly, all surfaces are exposed to enhance cleaning of the separate handles of the assembly. Alternatively, a locking pin can be provided to inhibit disassembly when desired.

Cleaning is also facilitated by provision of a leaf spring having a slot which engages a hook on the opposing handle. When the slot and hook are engaged, separation of the handle is inhibited; when disengaged, separation and disassembly is facilitated to accommodate cleaning.

Flanges are provided at the proximal end of the handle assembly and spaced a significant distance from the fulcrum. These flanges provide major surfaces which slide upon each other to facilitate alignment and stability of the handle assembly. With the flanges widely spaced from the fulcrum, a long moment arm is provided to enhance alignment of the assembly.

These flanges can be provided with slots which intersect each other at a point which moves along the assembly as the handles are opened and closed. The cartridge can be provided with a snap fitting, movable with an operating pin, which engages these slots at the point of intersection. In this manner the cartridge is provided with a snap fit at both its proximal end and its distal end in order to enhance engagement of the cartridge and the handle assembly.

The mechanism associated with operation of the cartridge is provided by these intersecting slots in the handle assembly. Since the assembly can be formed of metal and machined to a higher degree of tolerance, this structure offers a high degree of manufacturability and lower cost.

Overdrive protection is provided at opposing ends of the handle assembly. This protection is available not only between the handles but also between the handle assembly and the cartridge.

Palming is facilitated by providing handle bars with an increased spacing to inhibit slipping of the surgeon's fingers along the bars. Finger ridges are also provided to facilitate positioning of the fingers in this favored step of operation.

In one aspect of the invention, a surgical instrument includes a handle assembly, and an end effectors removably attached to the assembly and operable by the assembly. A second handle is pivotal on a first handle of the assembly at a fulcrum. A female bayonet fitting is disposed at the fulcrum on the first handle while a male bayonet fitting is disposed at the fulcrum on the second handle. These fittings have a first relative position permitting assembly and disassembly of the handles, and a second relative position permitting pivotal movement of the handles to facilitate operation of the end effector.

In another aspect of the invention, the fulcrum divides the handle assembly into a proximal end and a distal end. At the proximal end a pair of handle bars extend to the pair of finger rings and are disposed relative to each other to intersect at an imaginary apex other than the fulcrum.

In still another aspect of the invention, the first and second handles are pivotal at a fulcrum and relative to an axis, between an open position and a closed position. A first flange fixed to the first handle and extending inwardly toward the second handle, includes portions defining a first slot. Similarly a second flange, fixed to the second handle and extending inwardly toward the first handle, includes portions defining a second slot. The first slot is disposed at an angle to the second slot and intersects the second slot at a point of insertion which moves between the opened position and the closed position of the handles. An operating pin included in the cartridge is coupled to the slots at the point of intersection to operate the cartridge as the handles move between the opened position and the closed position. A snap fitting is coupled to the operating pin of the cartridge to engage the handle assembly at the point of intersection in a snap-fit relationship.

In a further aspect of the invention, the first flange has a first planar surface and the second flange has a second planar surface. These first and second planar surfaces slidingly engage each other to define a point of stability inhibiting movement of the first flange in a direction transverse to the second flange. This point of stability is spaced from a second point of stability, a distance greater than one-half the length of the clip applier.

In still a further aspect of the invention, overdrive protectors are included in the handle assembly for preventing pivoting of the handles beyond the closed position. A first pair of the overdrive protectors are disposed between the handles of the handle assembly. A second pair of the overdrive protectors is disposed between the handle assembly and the cartridge.

These and other features and advantages of the invention will become more apparent with a description of preferred embodiments and reference to the associated drawings.

DESCRIPTION OF THE DRAWINGS

FIGS. 5–7 are side elevation views illustrating a preferred method for mounting the disposable cartridge on the non-disposable handle assembly in a snap fit relationship;

FIG. 5 is a side elevation view of the cartridge being moved toward an operating position on the handle assembly;

FIG. 6 is a side elevation view illustrating a snap fit of the cartridge on the fulcrum of the handle assembly;

FIG. 7 is a side elevation view illustrating a snap fit relationship between the cartridge and the slots of the handle assembly;

FIG. 8 is a side view of a snap fitting carried by the operating pin of the cartridge and adapted for a snap fit into the slots of the handle assembly;

FIG. 9 is a bottom plan view of the snap fitting illustrated in FIG. 8;

FIG. 12 is a top side perspective view of the handles aligned for assembly or disassembly at a bayonet fitting disposed at the fulcrum of the assembly;

FIG. 13 is a perspective view of a female portion of the bayonet fitting illustrated in FIG. 12;

FIG. 14 is a perspective view of a male portion of the bayonet fitting illustrated in FIG. 12;

FIG. 18 illustrates a top plan view of three handles assemblies of the present invention adapted for use with a small-size clip and cartridge;

FIG. 19 illustrates three sizes of handle assemblies adapted for use with a medium-size clip and cartridge;

FIG. 20 illustrates two handle assemblies adapted for use with a medium-large clip and cartridge;

FIG. 21 illustrates two handle assemblies adapted for use with a large-size clip and cartridge.

DESCRIPTION OF PREFERRED EMBODIMENTS

Figure 1:
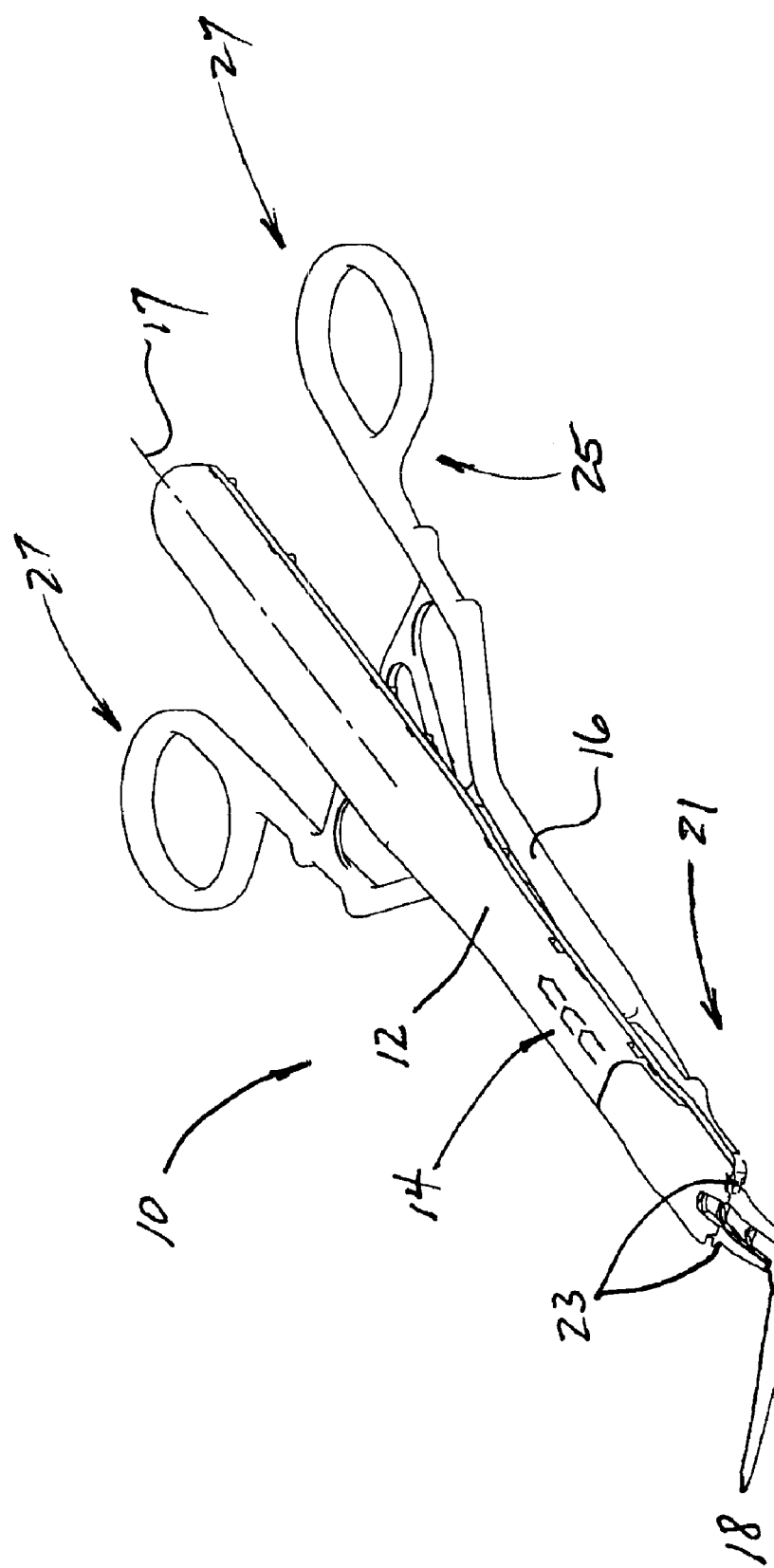
FIG. 1 is a top/side perspective view of a handle assembly and associated clip cartridge of the present invention.

A modular ligating clip applier is illustrated in FIG. 1 and designated by the reference numeral 10. A cartridge 12 containing a train of ligating clips 14 is removably carried on and operated by a handle assembly 16 having an axis 17. Jaws 18, carried by the cartridge 12, are adapted to receive the clips, one at a time, and to crimp the received clip onto body tissue, such as a blood vessel of a patient.

Movement of the jaws 18 from the normally opened state to the closed state is accomplished by operation of the handle assembly 16 which, in a preferred embodiment, has a scissors configuration. The handle assembly 16 has a distal end 22 terminating in a pair of pawls 23 and a proximal end 25 terminating in a pair of finger rings 27. The pawls 23 extend outwardly of the jaws 18 and are operable by closing the finger rings 27 to move the jaws 18 from the normally opened position to the closed position.

A modular ligating clip applier of this type is illustrated and described in U.S. patent application Ser. No. 60/117,079 filed on Jan. 25, 1999 and entitled "Modular Ligating Apparatus and Method" and in PCT/US00/01296 filed on Jan. 19, 2000 and entitled "Modulating Ligating Apparatus and Method." This application is incorporated herein by reference.

Figure 3:
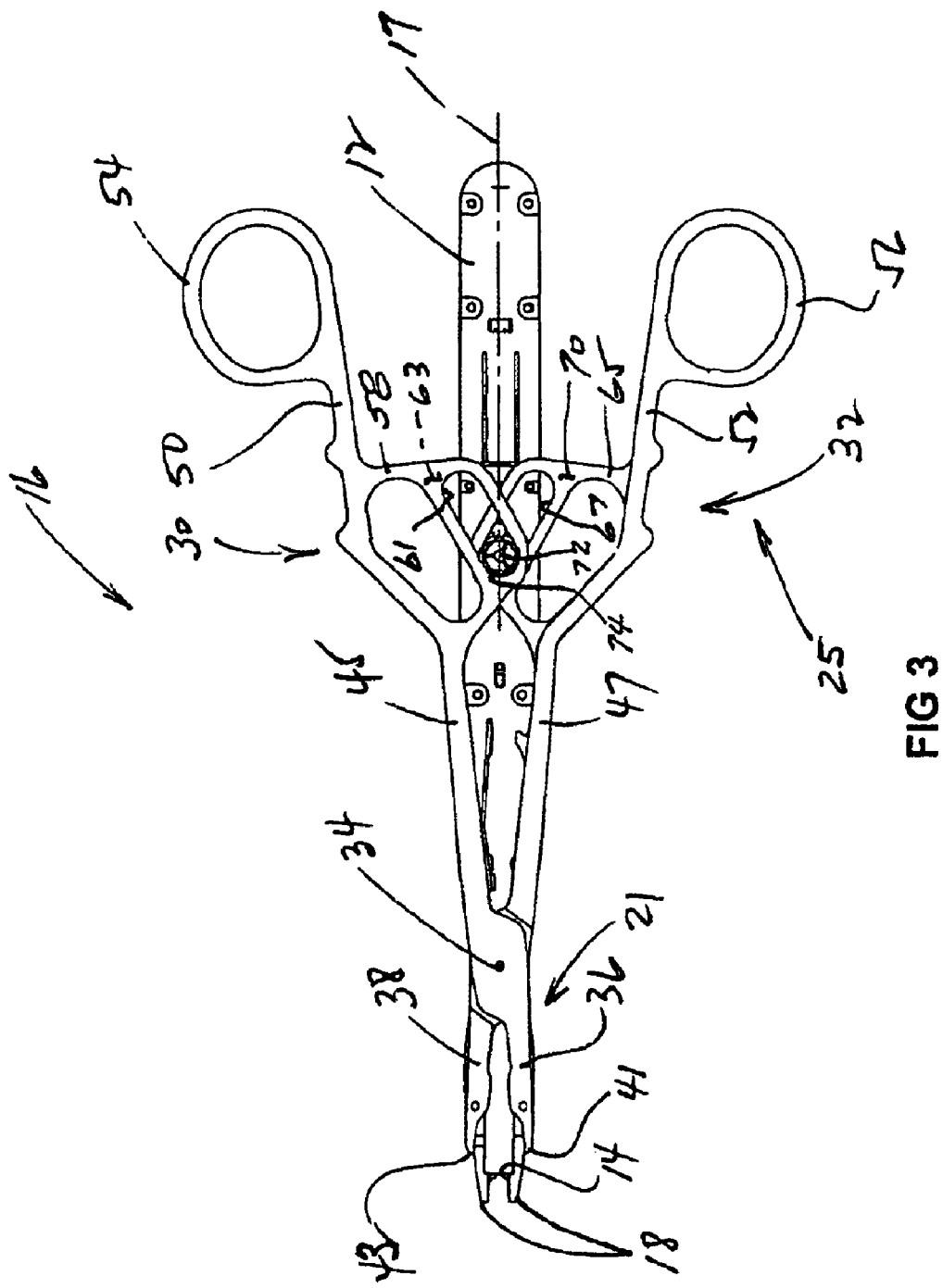
FIG. 3 is a bottom plan view of the clip applier illustrated in FIG. 1.

The scissors configuration of the handle assembly 16 is best illustrated in the bottom plan view of FIG. 3. In this view, it can be seen that the handle assembly 16 includes handles 30 and 32 which are pivotally attached to each other at a fulcrum 34. At the distal end 21, distally of the fulcrum 34, the handles 30 and 32 include a pair of arms 36 and 38, which extend to associated pawls 41 and 43, respectively.

At the proximal end 25, proximally of the fulcrum 34, the handles 30 and 32 include a pair of legs 45 and 47 which are generally aligned with the associated arms 36 and 38. Disposed proximally of the legs 45 and 47 are a pair of handle bars 50 and 52 which extend to associated finger rings 54 and 56, respectively.

In this embodiment, the handle 30 has a flange 58 which extends inwardly of the leg 45 and the handle bar 50. The flange 58 includes a slot 61 and a surface 63 which faces the cartridge 12. Similarly, the handle 32 includes a flange 65 which extends inwardly of the leg 47 and the handle bar 52. The flange 65 includes a slot 67 and a surface 70 which faces away from the cartridge 12. With the flange 65 positioned between the cartridge 12 and the flange 58, the surfaces 63 and 70 can be maintained in sliding engagement to provide increased stability for the handle assembly 16 in a manner discussed in greater detail below.

The slots 61 and 67 in this embodiment are generally straight and disposed at a common angle relative to the axis 17. As the handles 30 and 32 pivot on the fulcrum 34, the slots 61 and 67 intersect at a point which moves progressively along the axis 17. A button or snap 72 coupled to an operating pin 74 of the cartridge 12, can be snap fit into the slots 61 and 67 at this point of intersection.

It can not be seen that when the jaws 18 of the cartridge 12 are biased to the open state as illustrated in FIG. 3, the pawls 41 and 43 are moved outwardly to separate the arms 36 and 38. On the opposite side of the fulcrum 34, this causes the legs 45 and 47 to separate along with the handle bars 50 and 52 and the finger rings 54 and 56. Importantly, the point of intersection of the slots 61 and 67 is moved distally, as illustrated in FIG. 3, carrying the snap 72 and the operating pin 74 of the cartridge 12 to its distal most position. As the operating pin 74 approaches this location, the clip 14 is moved into its operating position between the jaws 18.

When the surgeon grips the handles 30 and 32, and moves them from this open state to a closed or proximate state, the finger rings 54 and 56 move toward each other as do the handlebars 50 and 52, and the legs 45 and 47. On the opposite side of the fulcrum 34, this movement to the closed position causes the arms 36 and 38 to move toward each other along with the pawls 41 and 43. The inwardly directed force of the pawls 41 and 43 causes the jaws 18 to close on the clip 14 thereby crimping the clip onto the body tissue. It will be noted that during this movement from the opened state to the closed state, the point of intersection between the slots 61 and 67 moves proximally along the axis 17. This movement which is followed by the snap 72 carries the operating pin 74 of the cartridge 12 to its proximal most position, thereby cycling the cartridge 12 to move the next clip 14 into the jaws 18.

Figure 4:
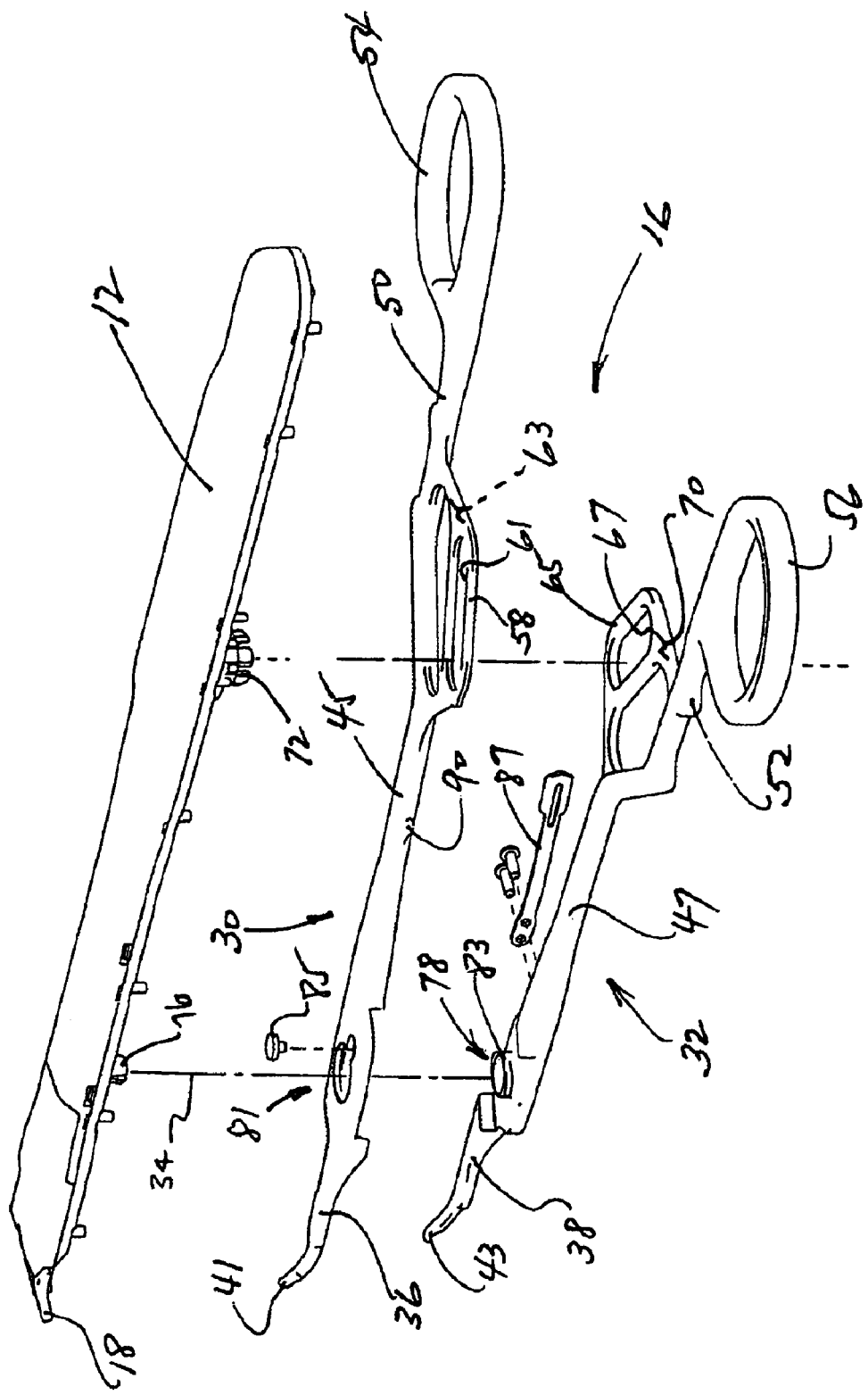
FIG. 4 is an exploded view of the clip applier illustrating separate handles associated with the handle assembly of the present invention.

The separate handles 30 and 32 and the cartridge 12, are illustrated in greater detail in the exploded view of FIG. 4. In this view, it an be seen that the jaws 18 and snap 72 are carried by the cartridge 12 along with a projection 76. When the cartridge 12 is mounted on the handle assembly 16, this projection 76 is maintained in a snap-fit relationship with a bayonet fitting disposed at the fulcrum 34. In the illustrated embodiment, this bayonet fitting includes a male component 78 carried by the handle 32, and a female component 81 carried by the handle 30. The bayonet fitting, which is discussed in greater detail below, defines a hole 83 into which the projection 76 can be snapped fit when the cartridge 12 is mounted on the handle assembly 16. A locking pin 85, leaf spring 87 and associated hook 90, also illustrated in FIG. 4, are discussed in greater detail below.

A preferred method for mounting the cartridge 12 on the handle assembly 16 is illustrated in the progressive views of FIGS. 5–7. In FIG. 5, the cartridge 12 and handle assembly 16 are shown to be aligned and ready for engagement. In FIG. 6, the jaws 18 are positioned between the pawls 41 and 43. The remainder of the cartridge 12 is positioned over the axis 17 as shown in the plan view of FIG. 2. As the proximal end of the cartridge 12 is pivoted downwardly onto the handle assembly 16, the projection 76 on the cartridge 12 snaps into the hole 83 on the handle assembly 16. Further pivotal movement of the cartridge 12 will cause the snap 72 and associated operating pin 74 to snap into the slots 61 and 67 at their point of intersection, as illustrated in FIG. 3. In this ultimate position shown in FIG. 7, the cartridge 12 is generally parallel to the plane of the handle assembly 16 with the cartridge 12 supported in a removable snap-fit relationship by the projection 76 and the snap 72. In a preferred embodiment, these points of connection defined by the projection 76 and snap 72 are widely separated by a distance greater than about one-half the length of the cartridge 12. This aids in stabilizing the cartridge 12 on the handle assembly 16 in the operative position illustrated in FIG. 7.

The configuration of the button or snap 72 is illustrated in a preferred embodiment shown in the enlarged views of FIGS. 8 and 9. In this embodiment, the snap 72 is movable on the cartridge 12 which includes a bottom plate 92 and cover 94. The operating pin 74 of the cartridge 12 is moveable in a slot 97 which extends through the bottom plate 92 and provides the pin 74 with access into the cover 94.

The snap 72 can be formed with a flange 96 which is integral with a set of inwardly biased teeth 98 and outwardly biased fingers 101. During assembly of the cartridge 12, the snap 72 can be snap-fit onto the pin 74, with the teeth 98 engaging the pin 74 preferably in a non-removable relationship. In this state, the flange 96 of the snap 72 is slidable along with the operating pin 74 along the bottom plate 92. The fingers 101 of the snap 72 are biased outwardly with ridges which removably engage the slots 61 and 67 of the handle assembly 16 at their point of intersection, as best illustrated in FIG. 3.

Figure 11:
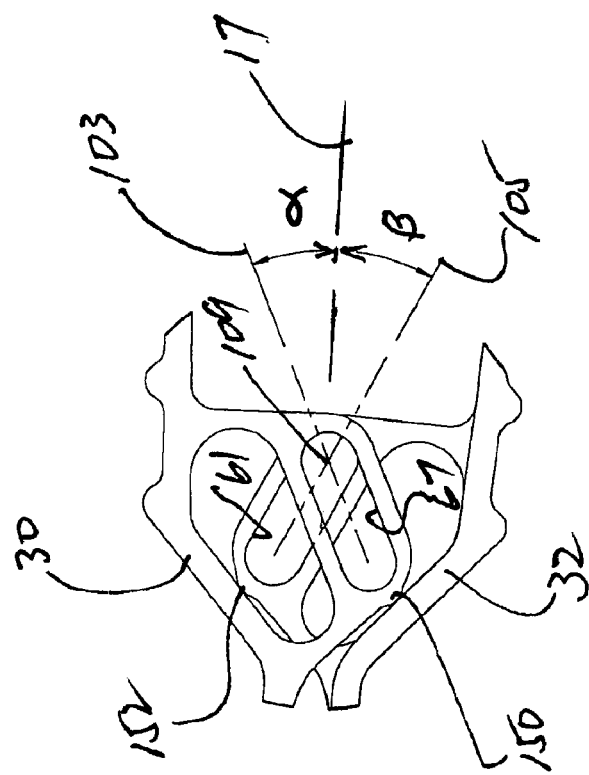
FIG. 11 is a top plan view similar to FIG. 10 and showing the handles of the assembly in a closed state.
Figure 10:
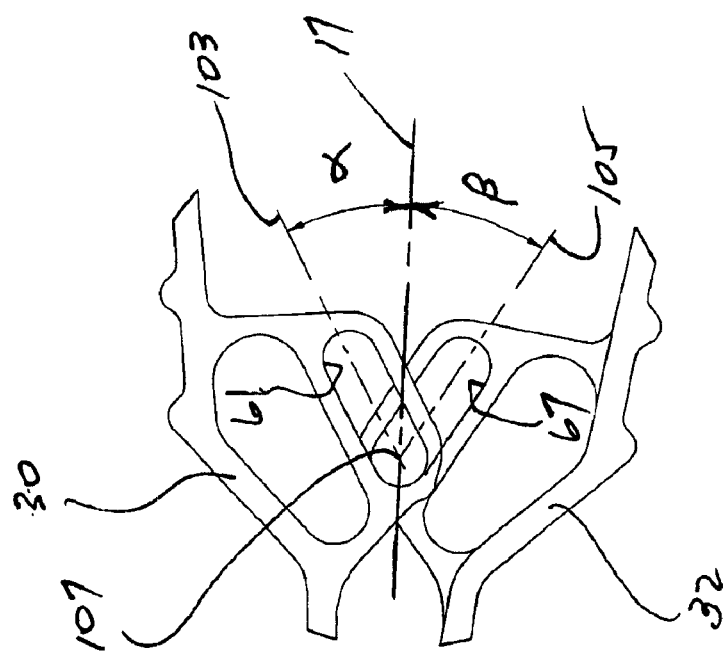
FIG. 10 is a top plan view of the flanges and associated intersecting slots associated with the handle assembly, the handles of the assembly being shown in an open state.

Operation of the slots 61, 67 and the commensurate movement of the snap 72 and operating pin 74 (FIG. 3) can be better understood with reference to FIG. 10 wherein the handle assembly 16 is shown in the opened state, and FIG. 11 wherein the handle assembly 16 is shown in the closed state. In this embodiment, the slots 61 and 67 are generally straight and extend along respective axes 103 and 105. The slot 61 of the handles can be angled proximally and outwardly to define an angle $\alpha$ between the axis 17 of the handle assembly 16 and the axis 103 of the slot 61. Similarly, the slot 67 of the handle 32 can be angled proximally and outwardly to define an angle $\beta$ between the axis 17 of the handle assembly 16 and the axis 105 of the slot 67. In this preferred embodiment, the slots 61 and 67 are shown to intersect at a distal point of the intersection 107 which defines the distal most position for the snap 72 and operating pin 74.

As the handles 30 and 32 are moved to their closed position illustrated in FIG. 11, the point of intersection defined by the slots 61 and 67 moves from the distal point of intersection of 107 toward a proximal point of intersection 109. In this closed position of the handles 30, 32, the proximal point of intersection 109 defines the proximal-most position of the snap 72 and operating pin 74. Thus by operation of the handles 30 and 32, the pin 74 of the cartridge 12 can be moved along the axis 17 between the points 107 and 109.

In this embodiment, the slots 61 and 67 pivot with the associated handles 30 and 32 on the fulcrum 34 as illustrated in FIG. 3. As a result, the angles α and β, measured between the axis 17 and the respective axes 103 and 105, will vary as the handles 30, 32 are moved between the opened position (FIG. 10) and closed position (FIG. 11). For example, in a preferred embodiment, the sum of the angles α and β in the opened position is equal to about 59 degrees. In the closed position, the sum of the angles α and β is equal to about 49 degrees.

From the foregoing embodiment, it can be appreciated that the shapes of the slots 61 and 67, their relative positions, and their positions relative to the axis 17, dictate the timing, direction and velocity of movement for the pin 74. In the illustrated embodiment wherein the slots are disposed at equal angles α and β relative to the axis 17, and the slot 61 and 67 are straight, the pin 74 will move at a generally constant rate between the points 107 and 109. In other embodiments, the slots 61 and 67 may have different shapes, may be cured, or may have different relationships with respect to the axis 17. By changing the size, shape and direction of the slots 61, 67 not only with respect to each other, but also with respect to the axis 17, movement of the snap 72 and pin 74 can be highly controlled, not only along the axis 17, but also laterally of the axis 17.

The exploded view of FIG. 12 shows the structure and method associated with assembling the handles 30 and 32 of the handle assembly 16. The structure of the bayonet fittings 78 and 81 associated with the handles 32 and 30, respectively, are of particular interest in FIG. 12 and the enlarged views of FIGS. 13 and 14. For example, with reference to FIG. 13, it can be seen that the female fitting 81 can be formed in a section 112 of the handle 30 which has been machined to provide a reduced thickness and an alignment surface 114. In this case, the female fitting 81 can be formed as a circular hole with a pair of flanges 116 extended into the hole from opposite directions. Each of these flanges is provided with an outwardly facing shoulder 118 which engages the male fitting 78.

On the opposite handle 32, a similar section 121 can be formed with a reduced thickness and an inwardly facing alignment surface 123. Extending from the inwardly facing surface 123, the male fitting 78 is provided with the configuration of a cylinder 125 which defines the interior hole 83 for the projection 76 (FIG. 4). Extending outwardly of the cylinder 125 are a pair of opposing flanges 127 and 130.

With this construction for the male and female fittings 78 and 81, respectively, the handles 30 and 32 can be positioned as illustrated in FIG. 12 at a relative angle such as 110 degrees so that the flanges 127 and 130 of the male fitting 78 can be received between the flanges 116 of the female fitting 81.

Figure 15:
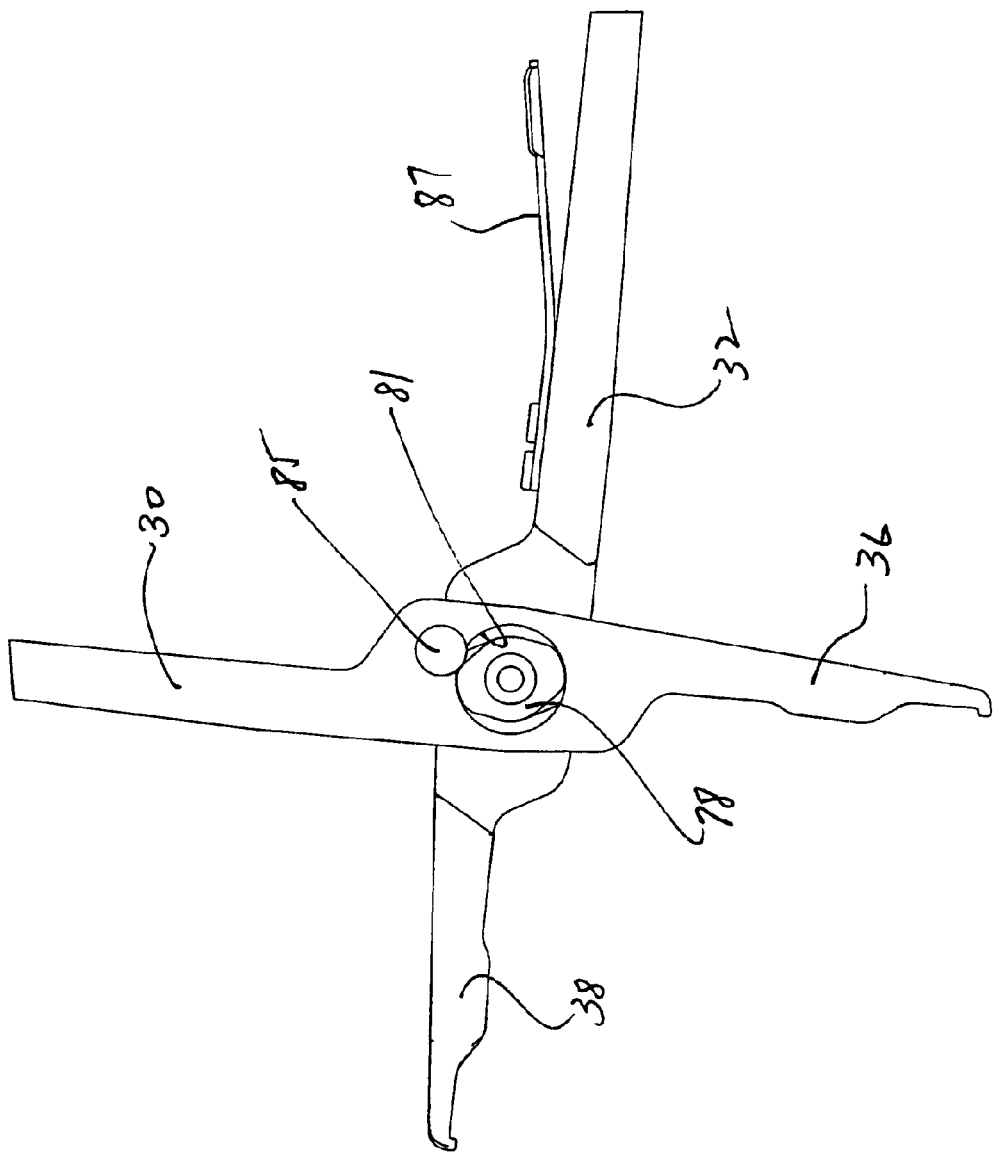
FIG. 15 is a top plan view of the bayonet fitting showing the handles aligned for assembly and further illustrating a locking pin to inhibit disassembly.
Figure 16:
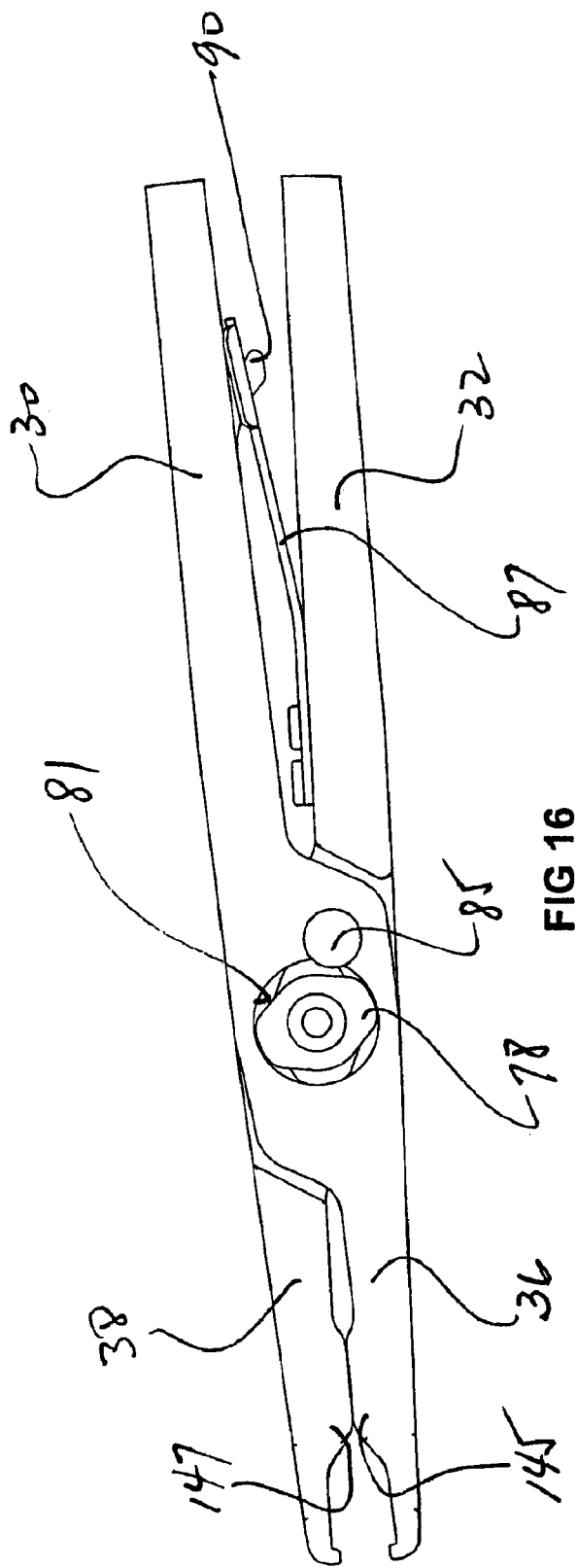
FIG. 16 is a top view similar to FIG. 16 and showing the handle assembly in a closed operating position.

Once the male fitting 78 has been aligned with the female fitting 81 as illustrated in FIG. 12, the handles 30 and 32 can be moved toward the closed position as illustrated in FIG. 15. With this pivotal movement, the flanges 127 and 130 associated with the male fitting 78 will ride along the shoulders 118 associated with the flanges 116 of the female fitting 81. Ultimately the handles 30 and 32 can be moved to the closed position as illustrated in FIG. 16.

The resulting alignment of these major surfaces 114 and 123 greatly enhances the stability of the handle assembly 16. This stability is even further enhanced by the sliding relationship of the surfaces 63 and 70 associated with the flanges 58 and 65, respectively. Even more important is the relationship of the associated surfaces 114 and 123 relative to the associates surfaces 63 and 70. These associated surface pairs are widely separated along the length of the handle assembly 16 in order to define a long moment arm between the surface pairs. This greatly enhances the structural stability and commensurate alignment of the handles 30 and 32.

Of particular advantage to the present invention is the fact that the bayonet fittings 78 and 81 not only provide a high level of structural but also facilitate both assembly and disassembly of the handles 30 and 32. Disassembly can be of particular interest in the cleaning of the handles 30 and 32. By separating the fittings 78 and 81, all surfaces of the handles 30 and 32 are exposed so that there are no hidden compartments containing contaminants or debris.

In a preferred embodiment, a pin hole 132 can be provided as illustrated in FIG. 13. This hole is sized and configured to receive the locking pin 85 (FIG. 4) which extends slightly into the circular opening associated with the female fitting 81. When the bayonet fittings 78 and 81 are assembled as illustrated in FIG. 15, the pin 85 can prevent disassembly of the handles 30 and 32 if that feature is preferred in a particular embodiment. In FIG. 16 the pin 85 is shown with the bayonet fittings 78 and 81 and the handles 30 and 32 in the closed position.

FIG. 16 also illustrates another aspect of the present invention wherein the leaf spring 87 on the handle 32 engages the hook 90 on the handle 30. This leaf spring 87 biases the handles 30 and 32 toward the open state. As the handles 30 and 32 separate, the hook 90 rides within a slot at the proximal end of the leaf spring 87. In a preferred embodiment, this slot is closed; so the leaf spring 87 and associated hook, when engaged, will limit further separation of the handles 30 and 32. However, in order to accommodate complete separation of the handles 30 and 32 for cleaning purposes, the lead spring 87 can be removed from the hook 90 as illustrated in FIG. 12.

Figure 17:
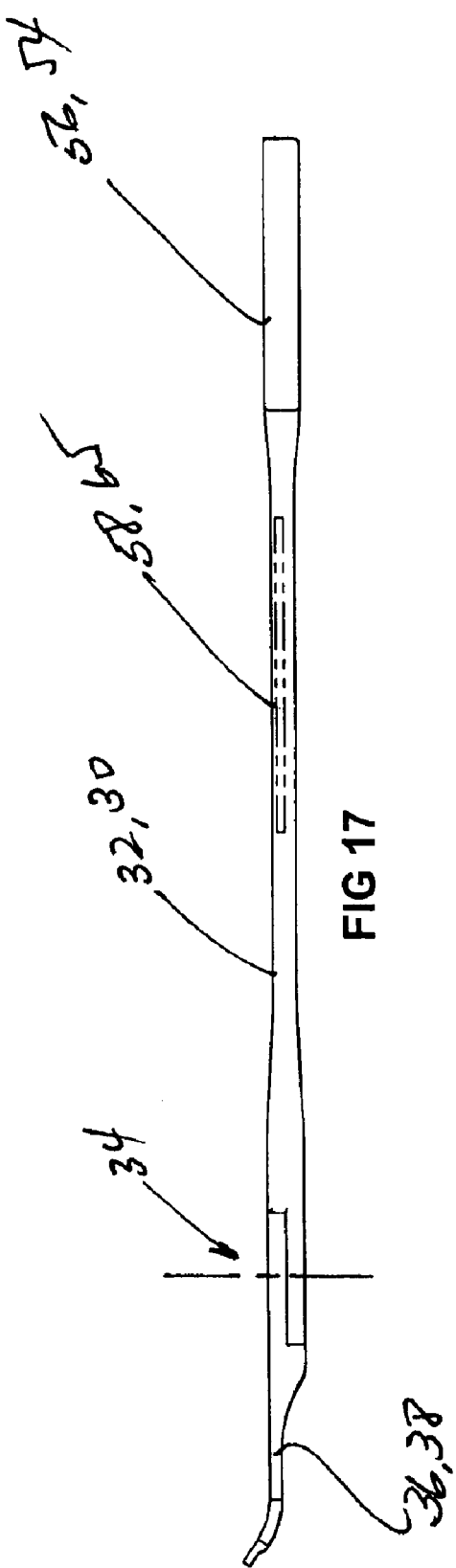
FIG. 17 is a side elevation view of the handle assembly illustrating areas of increased thickness facilitating stability of the assembly and comfort for the user.

Another aspect of the invention is illustrated in the side elevation view of FIG. 17. From this drawing it can be seen that a preferred embodiment of the handle assembly 16 provides for areas of increased thickness and areas of decreased thickness. This particular structure provides increased balance and improved tactile feedback for the surgeon. It has been found that by increasing the thickness of the handle assembly 16 in the areas of the fulcrum 34 and the finger rings 54 and 56, greater balance can be achieved for the instrument. This provides a reduced area of thickness between the two increased areas of thickness and thereby improves the balance and feel of the instrument. In a preferred embodiment, the thickness of the handle assembly 16 at the fulcrum 34 is about 3/16 inch. This same thickness is maintained at the finger rings 54 and 56. In the region between these two areas, the handles 30 and 32 are provided with a reduced thickness such as 1/8 inch to balance the instrument.

Figure 2:
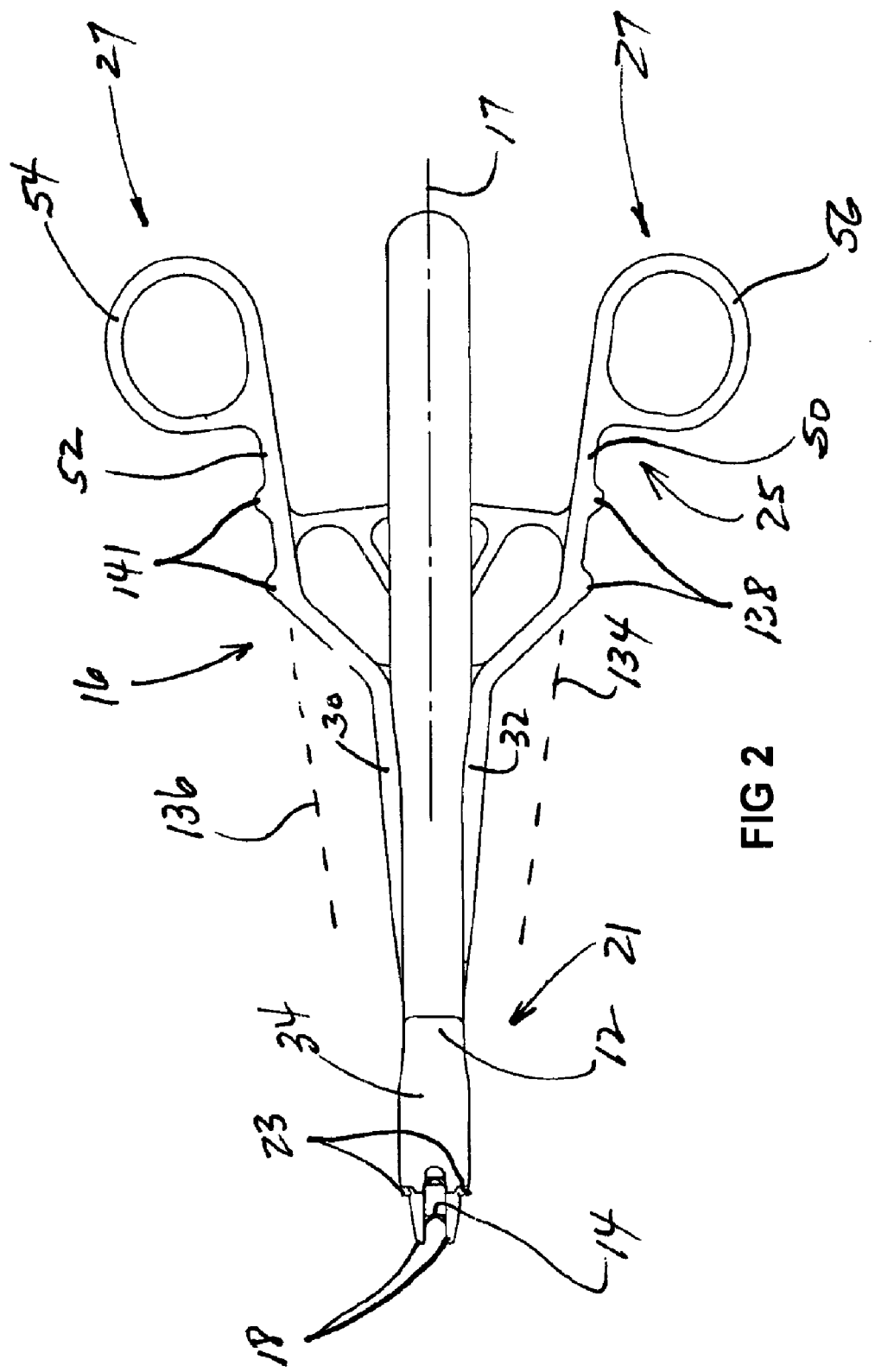
FIG. 2 is a top view of the clip applier illustrated in FIG. 1.

Another feature of the present invention is associated with the handle bars 50 and 52, perhaps best illustrated in FIG. 2. It has been found that many of the surgeons using modular clip appliers, operate the device by "palming" the handle assembly. Rather than placing their fingers within the finger rings 54 and 56, the handles are engaged by the palm of the hand. With this orientation the fingers extend along one of the handles, such as the handle 30, while the thumb extends along the other handle, such as the handle 32. In order to facilitate palming of the present handle assembly 16, the legs 45 and 47 which intersect at the fulcrum 34, do not extend in straight lines to the finger rings 54 and 56, respectively. Rather, these legs 45 and 47 diverge outwardly to the handle bars 50 and 52 respectively, which then extend to the finger rings 54 and 56. These handle bars 50 and 52, which may also be straight in configuration, are disposed on imaginary lines 134 and 136, respectively which converge distally to a point that is distal of the fulcrum 34. This structure provides the handles 30 and 32 with a remote configuration near the fulcrum 34, which facilitates reaching into narrow areas of the body. More proximally, near the finger rings 54 and 56, the handles 30 and 32 have a wider construction at the handle bars 50 and 52 which facilitates the palming aspect of the present invention. This wider configuration is achieved even though the handle bars 50 and 52 may be parallel to the legs 32 and 30, respectively. Ridges 138 and 141 can be provided along the respective handle bars 50 and 52 in order to facilitate finger placement and inhibit sliding of the handle assembly 16 in the user's hand.

The clips 14 are traditionally provided in four different sizes: a small clip having a width of about ⅛ inch; a medium clip having a width about ³⁄₁₆ inch; a medium-large clip having a width of about ¼ inch; and a large clip having a width approaching ⅜ inches. These four clips are illustrated in the respective views of FIGS. 18, 19, 20 and 21 where elements of similar structure are designated by the same reference numeral followed by the respective lower-case letters "a", "b", "c", and "d". Thus, in FIG. 18 the clip is designated by the reference numeral 14a while in FIG. 21 the clip is designated by the reference numeral 14a.

Since the position of the operating pin 74a relative to the jaws 18a may vary with the different clip sizes, a dedicated group of handle assemblies 143a may be desired for each of the clips and its associated cartridge. Such a group is designated by the reference numeral 143a in FIG. 18. In this view it will be noted that the small clip 14a can be housed in a small cartridge 12a having a length such as six inches. In order to accommodate this size of clip 14a and cartridge 12a, the dedicated handle assemblies may include a short handle assembly 16a, a medium handle assembly 16a', and a long handle assembly 16a".

Since the short handle assembly 16a makes it easier to manipulate the cartridge 12a, and since the long handle assembly 16a" makes it easier to reach into remote locations, the group of dedicated handle assemblies 143a will enable a user to select a handle assembly which is sufficiently long to reach the operative site but sufficiently short to maximize manipulation of the cartridge 12a. In a preferred group of the dedicated handle assemblies 143a, the short handle assembly 16a has the length of about six inches, the medium handle assembly 16a" has a length of about 8 inches, and the long handle assembly 16a" has the length of about 11 inches.

Figure 18:
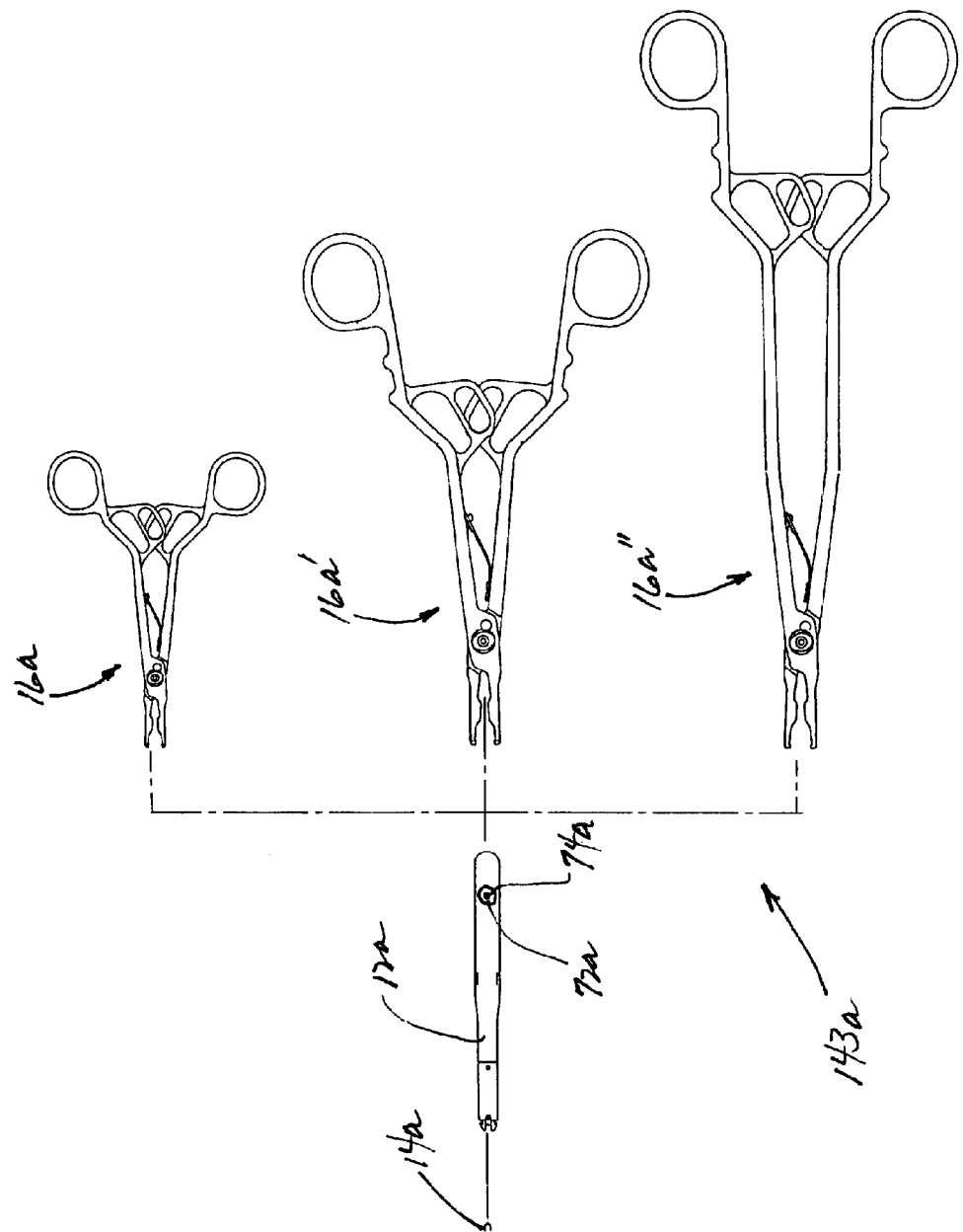
FIG. 18–FIG. 21 illustrates top plan views of various sizes of handle assemblies adapted for use with various sizes of cartridges and clips.
Figure 19:
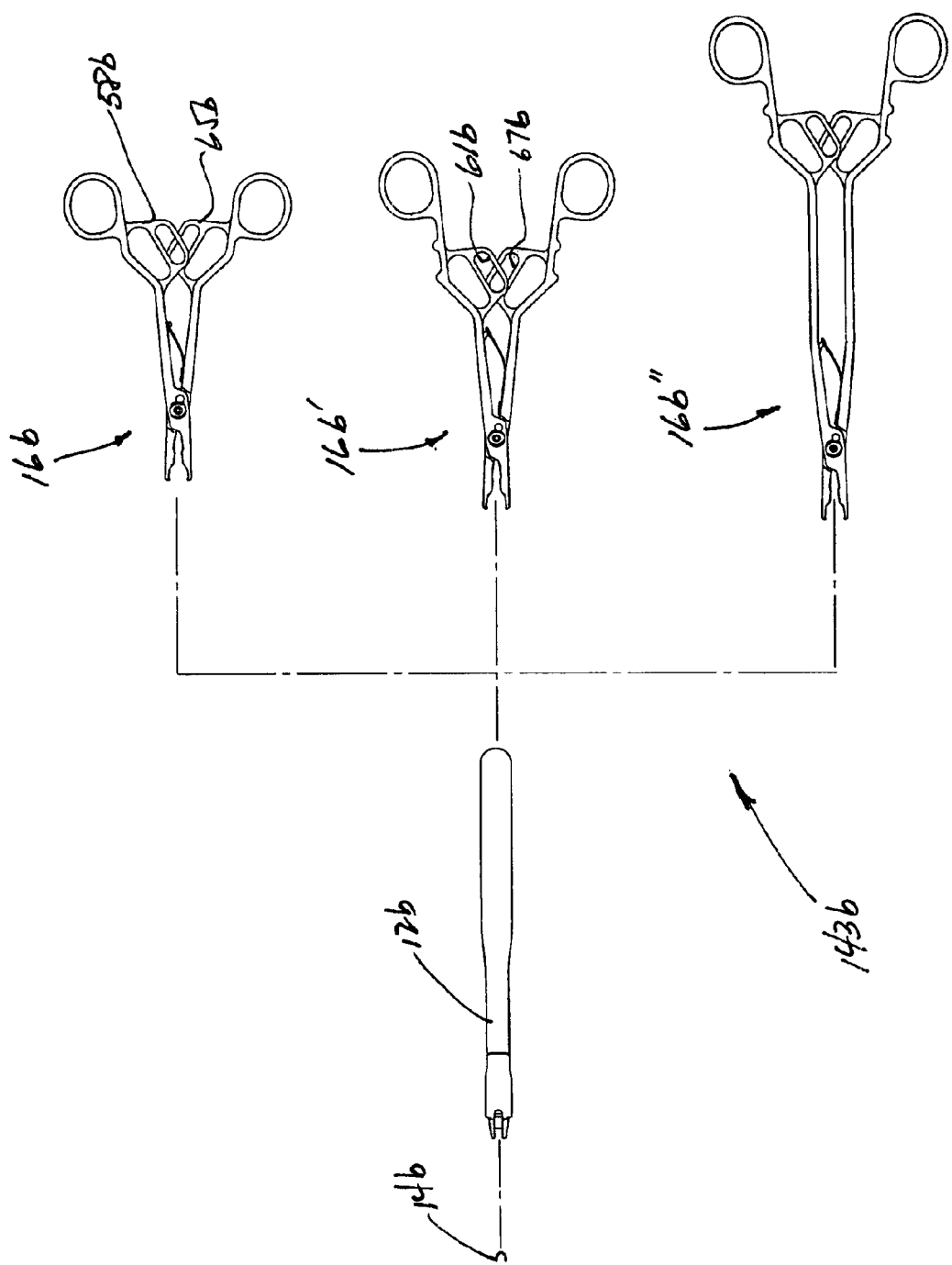

With reference to FIG. 19, it will be noted that the medium-sized clip 14b is capable of being housed in the cartridge 12b having a length such as seven inches. The group of dedicated handle assemblies 143b includes a short handle assembly 16b, a medium handle assembly 16b' and a long handle assembly 16b". In order to accommodate the longer cartridge 12b, each of the handle assemblies in the group 143b will typically be longer than the associated handle assemblies in the group 143a (FIG. 18). Depending on the location and required travel for the operating pin 74b and associated snap 72b, placement of the flanges 58b and 65b and the associated slots 61b and 67b, may also vary.

Figure 20:
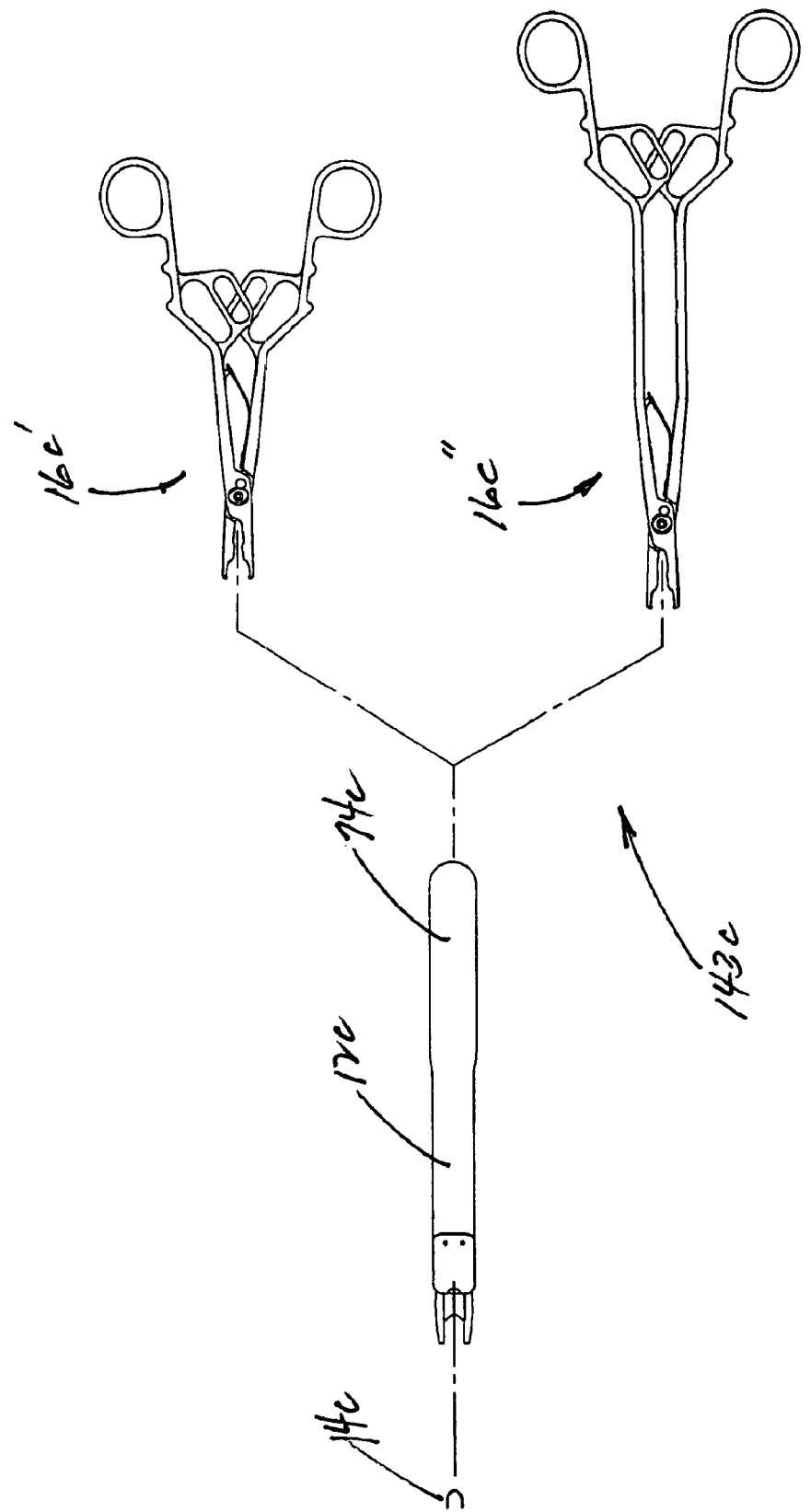

With reference to FIG. 20, it can be seen that the medium-large clip 14c is adapted to be carried in the cartridge 12c which may have a length of about 22.37 cm (8.809 in). This cartridge 12c can be adapted for use with a group of dedicated handle assemblies designated by the reference number 143c. These assemblies include a medium handle assembly 16c', and large handle assembly 16c". Once again, each of the handle assemblies in this group 143c may be longer than the associated assembly in the group 143b (FIG. 19).

Figure 21:
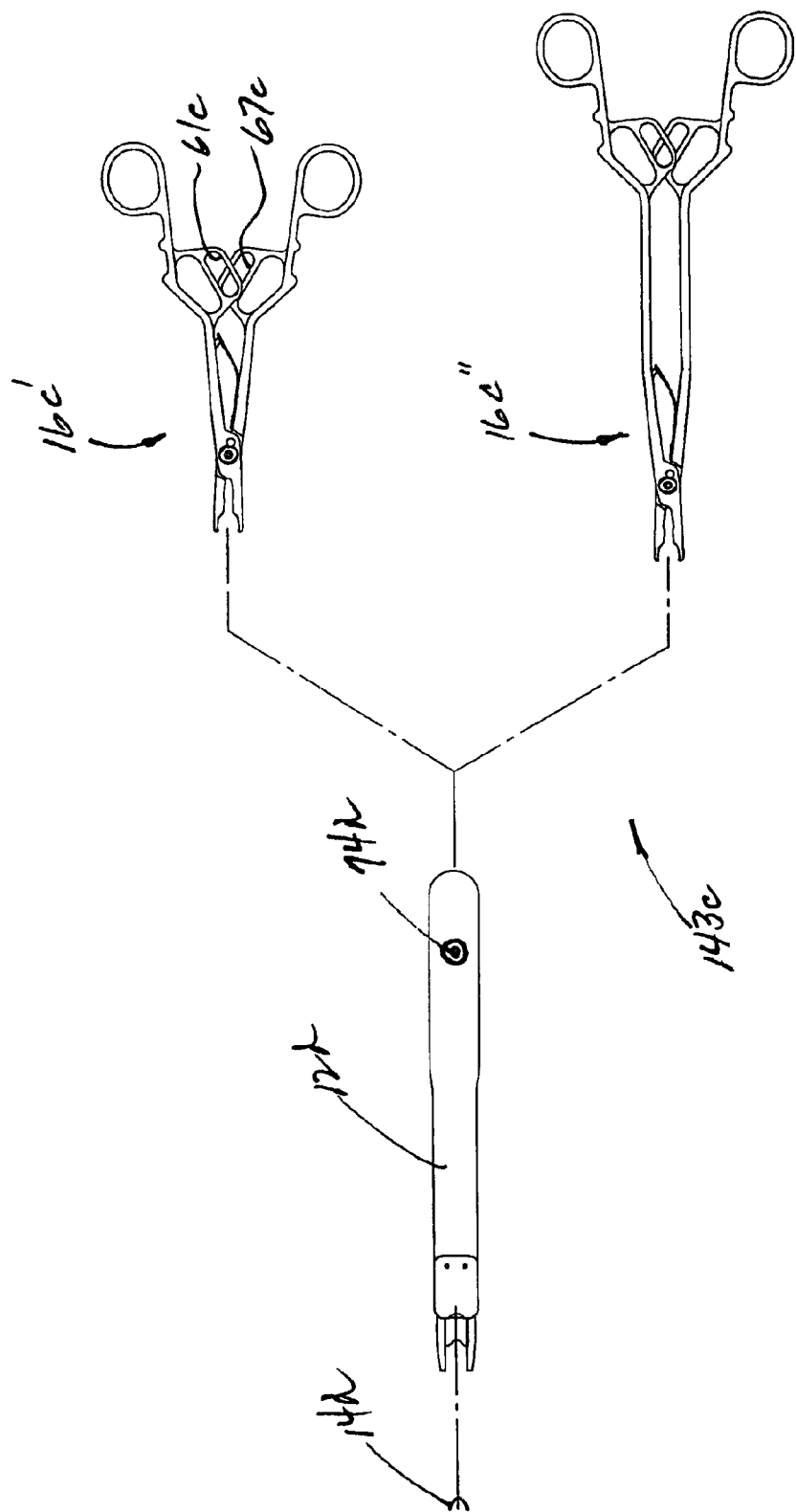

Although the large clip 14d illustrated in FIG. 21 can be carried in a cartridge 12d which is longer than the cartridge 12c (FIG. 20), the cartridge 12d may nevertheless be adapted for use with the same group of handle assemblies 143c previously discussed. Thus the handle assemblies 16c' and 16c" mentioned with respect to FIG. 20, can be used to operate the cartridge 12d illustrated in FIG. 21. This universal group 143c of handle assemblies can function with different sizes of the clips 14c and 14d, as well as the different sizes of cartridges 12c and 12d. Although the desired travel of the operating pin 74c may be shorter than that for the pin 74d, the slots 61c and 67c can be made sufficiently long to accommodate the pin 74d, with the pin 74c using less than the entire length of the slots 61c and 67c.

In another aspect of the invention, overdrive protection is provided in order to prevent closure of the handles 30 and 32 beyond the point required by the cartridge 12. In a preferred embodiment, this overdrive protection is provided in several locations. For example, with reference to FIG. 16, it will be noted that interfering lugs 145 and 147 can be provided on the respective arms 36 and 38. When these lugs 145 and 147 come into contact, further closure of the handles 30 and 32 is prevented.

Further overdrive protection can be provided by creating a lug on one of the handles 30 and 32 which has an interference fit with the other of the handles 30 and 32. For example, with reference to FIG. 11, lugs 150 and 152 are created on the associated handles 30 and 32. These lugs 150 and 152 have an interference fit with the opposing handle 32 and 30, respectively, at the point of maximum closure.

Even further overdrive protection can be provided between the cartridge 12 and the handle assembly 16. With the snap 72 located within the intersecting slots 61 and 67, as illustrated in FIG. 3, closure of the handles 30 and 32 will move the snap proximally to a proximal most point of intersection designated by the reference numeral 109 in FIG. 11. When the snap 72 reaches this fully closed position, an interference fit is provided between the snap 72 and the ends of the slots 61 and 67. This provides further overdrive protection that is even more directly related to the cartridge 12. With this overdrive protection, the handles 30 and 32 are inhibited from closing beyond a predetermined distance. This also ensures that the cartridge 12 is not driven beyond its desired ultimate position.

From the foregoing description of preferred embodiments, it can be appreciated that the concept of this invention is applicable to any surgical instrument having a handle assembly that can benefit from the increased stability and alignment characteristics previously discussed. Although the invention can be particularly appreciated in a surgical stapler, including a cartridge of staples removably attached to the handle assembly, this construction is merely representative of many surgical instruments having handle assemblies with end effectors.

Whether the end effector, such as the jaws of a staple cartridge are permanently or removable attached to the handle assembly, improved alignment and stability is always of interest. Other end effectors contemplated might include shears, scissors, graspers, clips, clamps and clinches, for example. In each of these cases, the end effector, such as the staple jaws 18, can be mounted on a disposable carrier, such as a staple cartridge that is removably attached to a non-disposable handle assembly.

In a broader sense, the invention contemplates a disposable portion and a non-disposable portion. Preferably the disposable portion, such as the cartridge 12, includes the end effectors, such as the jaws 18, and an associated structure for maintaining alignment of the end effectors. The non-disposable portion includes the handle assembly which can be sterilized, typically by autoclaving to facilitate repeated use of this non-disposable portion.

The disposable portion is intended to be carried by the non-disposable portion, as the cartridge 12 is carried by the handle assembly 16. More specifically, the cartridge 12 can be removably attached to the handle assembly 16 to facilitate assembly and disassembly of the disposable portion from the non-disposable portion. In a preferred embodiment, this attachment of the disposable portion to the non-disposable portion is accomplished without attaching the end effectors, such as the jaws 18, to either the arms 36, 38, or the pawls 41, 43. Rather, the end effectors are free to move or float relative to the arms 36, 38 and the pawls 41, 43. In this manner, the alignment of the end effector is dependent upon only the alignment structure within the disposable portion, such as the cartridge 12. With the jaws 18 floating relative to the arms 36, 38 and the pawls, 41, 43, their alignment is independent of the alignment of the handle assembly 16.

Since the handle assembly 16 is intended to be non-disposable, it is the structure most likely to receive severe treatment sometimes associated with the sterilizing or autoclaving process. This treatment is most likely to produce any misalignment associated with the combination. By making the alignment of the end effectors or jaws 18 independent of the alignment of the handle assembly 16, the primary cause of jaw misalignment can be avoided. Thus, the disposable portion or cartridge 12 is new to the combination each time the handle assembly 16 is used. This brings to the combination not only new end effectors, such as the jaws 18, but also new alignment structure for the end effectors. These characteristics of the combination are new with each disposable portion, and guarantee optimized performances with each use, regardless of any misalignment which may have resulted to the non-disposable portion such as the handle assembly 16.

Figure 22:
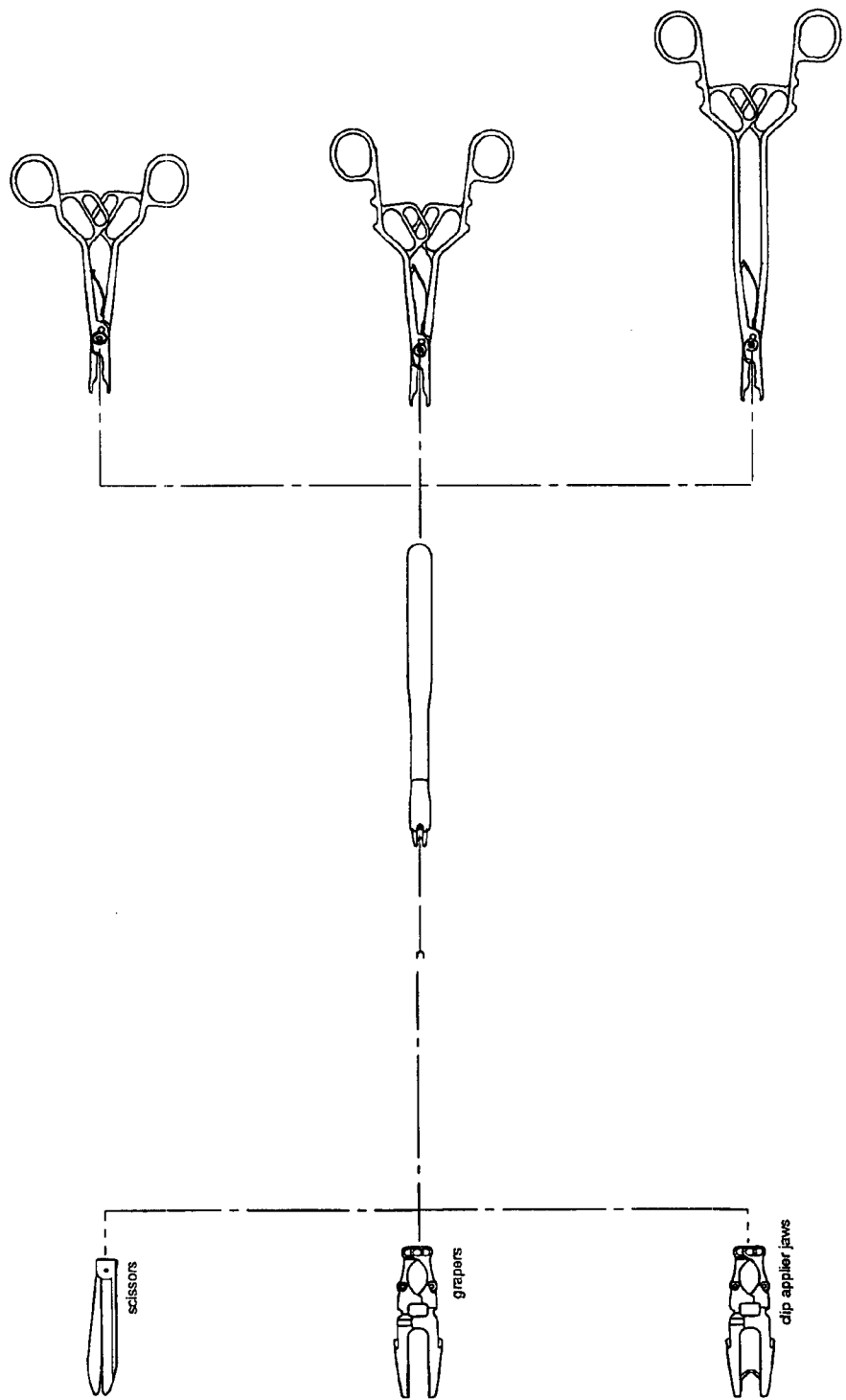
FIG. 22 is a top plan view of a handle assembly of the present invention adapted for alternative use with various end effectors.

To further illustrate this important aspect of the invention, attention is drawn to FIG. 22 which illustrates a handle assembly 16 adapted for alternative use with three types of end effectors, namely, a scissors end effector 160, a graspers end effector 162, and the clip applier end effector 165 which includes the jaws 18. In each case, the end effector has its own alignment structure. By way of example, the graspers end effector 162 includes grasper jaws 166 and an associated alignment structure 168. From this view, it can be further appreciated that misalignment of the handle assembly 16 will not effect the alignment of the jaws 166 which are independently aligned by the structure 168.

Many alterations and modifications can be made to the foregoing preferred embodiments without departing from the spirit and scope of the invention. Therefore it must be understood that the illustrated embodiments have been set forth only by way of example, and should not be taken as limiting the invention. For example, notwithstanding the fact that the claims set forth below recite certain elements and combinations, it must be expressly understood that the invention includes other combinations of fewer, more or different elements, which are not disclosed above even when not initially claimed in such combinations.

In addition, the words used in this specification to describe the invention and its various embodiments are to be understood not only in the sense of their commonly defined meanings but also in the sense of any special definitions used in this specifications, which may extend beyond the scope of the commonly defined meanings. Thus if an element can be understood in the context of this specification as including more than one meaning, than its use in the claims must be understood as being generic to all possible meanings supported by the specification and by the word itself.

The definitions of the words or elements of the following claims are, therefore, defined in the specification to include not only the combination of the elements which are literally set forth, but all equivalent structure, material or method steps for performing substantially the same function, in substantially the same way, to obtain substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter, now known or later devised, are expressly contemplated as being equivalently within the scope of the claims. Therefore, obvious substitutions now or later known to one with ordinary skill in the art are deemed to be within the scope of the defined elements.

The claims are thus to be understood to include what is specifically illustrated and described above, what is conceptually equivalent, what can be obviously substituted, and also what essentially incorporates the idea of the invention.

What is claimed is:

1. A surgical instrument, comprising:
 a handle assembly;
 an end effector carried by the handle assembly and operable by the handle assembly;
 a first handle included in the handle assembly;
 a second handle included in the handle assembly and pivotal on the first handle at a fulcrum;
 a female bayonet fitting disposed at the fulcrum on the first handle;
 male bayonet fitting disposed at the fulcrum on the second handle;
 the female bayonet fitting and the male bayonet fitting having a first relative position permitting assembly and disassembly of the first handle and the second handle, and a second relative position permitting pivotal movement of the first handle relative to the second handle to facilitate operation of the end effector.

2. The surgical instrument recited in claim 1, wherein:
 the handle assembly has an open position and a closed position; and
 the first relative position is in proximity to the open position.

3. The surgical instrument recited in claim 2, wherein:
 the second relative position is disposed between the open position and the closed position.

4. The surgical instrument recited in claim 1, wherein:

the female bayonet fitting includes first portions defining a whole and including a pair of first opposing flanges extending radially inwardly of the whole;

the male bayonet fitting includes second portions defining a cylinder and including a pair of second opposing flanges extending radially outwardly between the pair of first opposing flanges in the first relative position.

5. The surgical instrument recited in claim 1, further comprising:

means disposed on the handle assembly for inhibiting relative movement of the female bayonet fitting and the male bayonet fitting from the second relative position to the first relative position.

6. The surgical instrument recited in claim 5 wherein the inhibiting means comprises a pin fixed to the female bayonet fitting to inhibit pivotal movement of the male bayonet fitting to the first relative position.

7. The surgical instrument recited in claim 6 wherein the pin is removable from the female bayonet fitting to permit movement of the male bayonet fitting to the first relative position and thereby facilitate disassembly of the handle assembly.

8. The surgical instrument recited in claim 1 wherein the handle assembly is machined to form the female bayonet fitting and the male bayonet fitting.

9. The surgical instrument, comprising:

a handle assembly;

an end effector carried by the handle assembly and operable by the handle assembly;

a pair of handles included in the handle assembly and being pivotal relative to each other at a fulcrum which divides the handle assembly into a proximal end and a distal end;

a pair of finger rings included in the proximal end of the handle assembly;

a pair of handle bars included in the proximal end of the handle assembly, each of the handle bars extending more than one-half the distance between the fulcrum and an associated one of the finger rings;

the handle bars being disposed relative to each other to intersect at an imaginary apex other than the fulcrum.

10. The surgical instrument recited in claim 9, further comprising:

at least one ridge formed along one of the handle bars to facilitate finger placement when the instrument is palmed by a user.

11. The surgical instrument recited in claim 9, wherein:

the handle bars are disposed relative to each other to define a first angle at the imaginary apex when the handle bars are in a closed position and to define a second angle at the imaginary apex when the handle bars are in an opened position.

12. The surgical instrument recited in claim 11 wherein the imaginary apex moves proximately as the handle bars move from the closed position toward the opened position.

13. The surgical instrument recited in claim 12 wherein the imaginary apex is disposed distally of the fulcrum, in both the opened position and the closed position.

14. The surgical instrument recited in claim 9, further comprising:

a bayonet coupling disposed at the fulcrum and permitting pivotal movement of the handles at the fulcrum.

15. The surgical instrument recited in claim 9 wherein:

the handles have an intermediation disposed between the proximal end and the distal end; and the handles at the intermediate section have a cross sectional area less than that of the proximal end and the distal end.

16. A surgical instrument, comprising;

a non-disposable portion including a handle assembly with arms having first alignment characteristics;

a disposable portion carried by the handle assembly and including end effectors with second alignment characteristics;

the end effectors being disposed relative to the arms and having a floating relationship with the arms; whereby the second alignment characteristics of the end effectors are independent of the first alignment characteristics of the arms.

17. The surgical instrument recited in claim 16, wherein:

the non-disposable portion includes a fulcrum and;

the disposable portion is releasably attached to the non-disposable portion at the fulcrum.

18. The surgical instrument recited in claim 16 wherein the end effectors are disposed between the arms.

19. The surgical instrument recited in claim 16, wherein:

the end effectors include a first end effector and a second effector cooperating with the first end effector to produce an end effect; and the first end effector having a pivotal relationship with the second end effector.

20. The surgical instrument recited in claim 19, wherein:

the fulcrum of the non-disposable portion is a first fulcrum; and the first end effector pivots relative to the second end effector at a second fulcrum.

21. The surgical instrument recited in claim 20 wherein the first fulcrum is different from the second fulcrum.

22. The surgical instrument recited in claim 21 wherein the first fulcrum is spaced from the second fulcrum.

23. The surgical instrument recited in claim 22 wherein the first fulcrum has a first axis and the second fulcrum has a second axis different than the first axis.

* * * * *

UNITED STATES PATENT AND TRADEMARK OFFICE
CERTIFICATE OF CORRECTION

| | |
|---|---|
| PATENT NO. | : 6,896,683 B1 |
| APPLICATION NO. | : 09/675851 |
| DATED | : May 24, 2005 |
| INVENTOR(S) | : Donald L. Gadberry et al. |

It is certified that error appears in the above-identified patent and that said Letters Patent is hereby corrected as shown below:

On the title page: Item [73] Assignee:

The correct name of the assignee should be listed as Applied Medical Resources Corporation On the title page: Item [56], under Related U.S. Application Data, No. 63, it states: "Continuation" of application No. PCT/US00/01296, filed on Jan. 19, 2000.

The word "Continuation" should be replaced with the word --Continued-in-part-- of application No. PCT/US00/01296, filed on Jan. 19, 2000.

Signed and Sealed this

Thirtieth Day of January, 2007

JON W. DUDAS
*Director of the United States Patent and Trademark Office*